(12) United States Patent
Lin et al.

(10) Patent No.: US 7,979,150 B2
(45) Date of Patent: Jul. 12, 2011

(54) BIODEGRADABLE/BIORESORBABLE TISSUE AUGMENTATION/ RECONSTRUCTION DEVICE

(75) Inventors: Chia-Ying Lin, Ann Arbor, MI (US); Scott J. Hollister, Ann Arbor, MI (US)

(73) Assignee: The Regents Of The University Of Michigan, Ann Arbor, MI (US)

( * ) Notice: Subject to any disclaimer, the term of this patent is extended or adjusted under 35 U.S.C. 154(b) by 755 days.

(21) Appl. No.: 10/581,424

(22) PCT Filed: Dec. 3, 2004

(86) PCT No.: PCT/US2004/040298
§ 371 (c)(1), (2), (4) Date: Oct. 10, 2008

(87) PCT Pub. No.: WO2005/057165
PCT Pub. Date: Jun. 23, 2005

(65) Prior Publication Data
US 2009/0037148 A1 Feb. 5, 2009

Related U.S. Application Data

(60) Provisional application No. 60/527,455, filed on Dec. 5, 2003.

(51) Int. Cl.
*G06F 19/00* (2006.01)
(52) U.S. Cl. .............................. 700/98; 424/426; 606/77
(58) Field of Classification Search .................... 700/98, 700/120; 703/11; 45/69; 424/423, 426; 623/13.4; 606/77
See application file for complete search history.

(56) References Cited

U.S. PATENT DOCUMENTS

| | | | |
|---|---|---|---|
| 5,487,897 A | 1/1996 | Polson et al. | |
| 5,492,697 A | 2/1996 | Boyan et al. | |
| 5,527,864 A | 6/1996 | Suggs et al. | |
| 5,876,452 A | 3/1999 | Athanasiou et al. | |
| 6,203,573 B1 | 3/2001 | Walter et al. | |
| 6,511,511 B1 | 1/2003 | Slivka et al. | |
| 6,600,010 B2 | 7/2003 | Mao et al. | |
| 6,613,091 B1 | 9/2003 | Zdeblick et al. | |
| 6,783,712 B2 * | 8/2004 | Slivka et al. ..................... 264/51 |
| 2003/0006534 A1 | 1/2003 | Taboas et al. | |
| 2003/0069718 A1 | 4/2003 | Hollister et al. | |
| 2003/0075822 A1 * | 4/2003 | Slivka et al. ................. 264/45.3 |
| 2003/0108587 A1 | 6/2003 | Orgill et al. | |
| 2003/0175321 A1 | 9/2003 | Sapieszko et al. | |

OTHER PUBLICATIONS

Hollister, S. J.; Brennan, J. M.; Kikuchi, N; A Homogenization Sampling Procedure for Calculating Trabecular Bone Effective Stiffness and Tissue Level Stress, J. Biomechanics, vol. 27, No. 4, pp. 433-444, 1994.

* cited by examiner

*Primary Examiner* — Kidest Bahta
(74) *Attorney, Agent, or Firm* — Harness, Dickey & Pierce, P.L.C.

(57) ABSTRACT

A method of manufacturing biodegradable/bioresorbable tissue augmentation/reconstruction devices by defining material density distributions at selected time points during a material degradation lifecycle. These different density distributions are then superposed using general linear and/or non-linear functions that could include both time and degraded base stiffness weighting factors. The material density distribution may be created using topology optimization, image-based design or computed aided design methods to create a degradable device that retains sufficient physical properties (ie modulus, strength, electrical conductivity, thermal conductivity) through the material degradation lifecycle process. Thus, any bulk degrading material can be designed using this process for any tissue augmentation/reconstruction application.

20 Claims, 8 Drawing Sheets

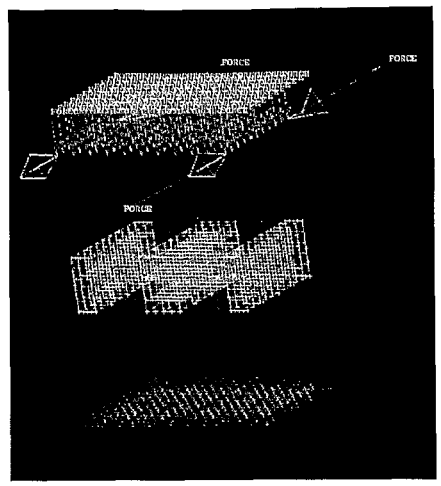
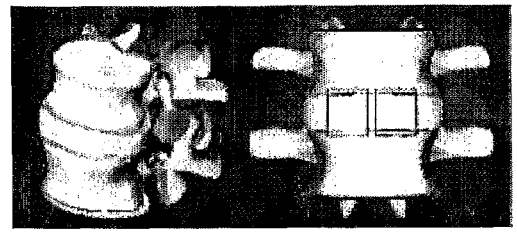
FIG. 6
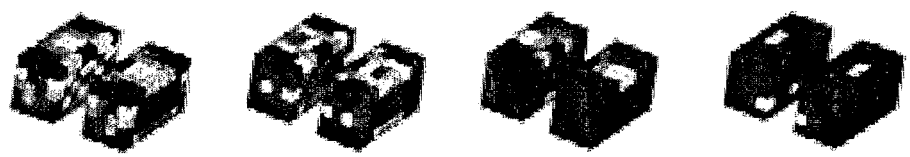
a　　　　　　　b　　　　　　　c　　　　　　　d
FIG. 7
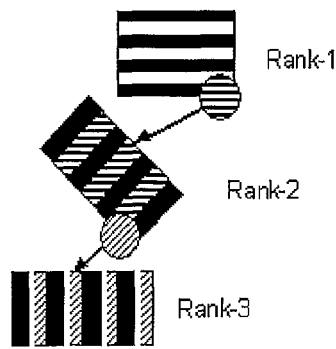
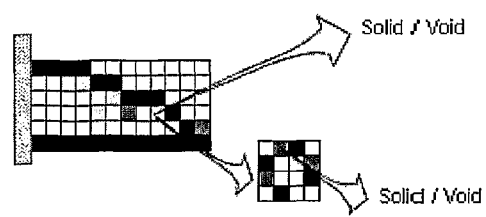
FIG. 8　　　　　　　　　　　FIG. 9

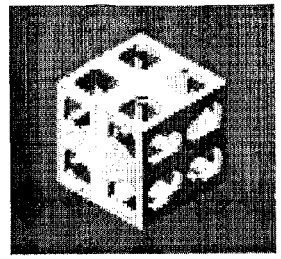
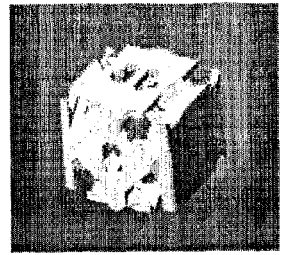
FIG. 16(a)　　　　　　　　　FIG. 16(b)
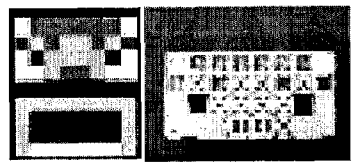
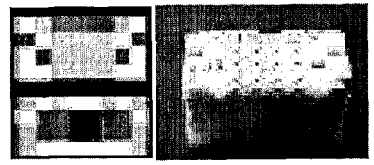
FIG. 17(a)　　　　　　　　　FIG. 17(b)
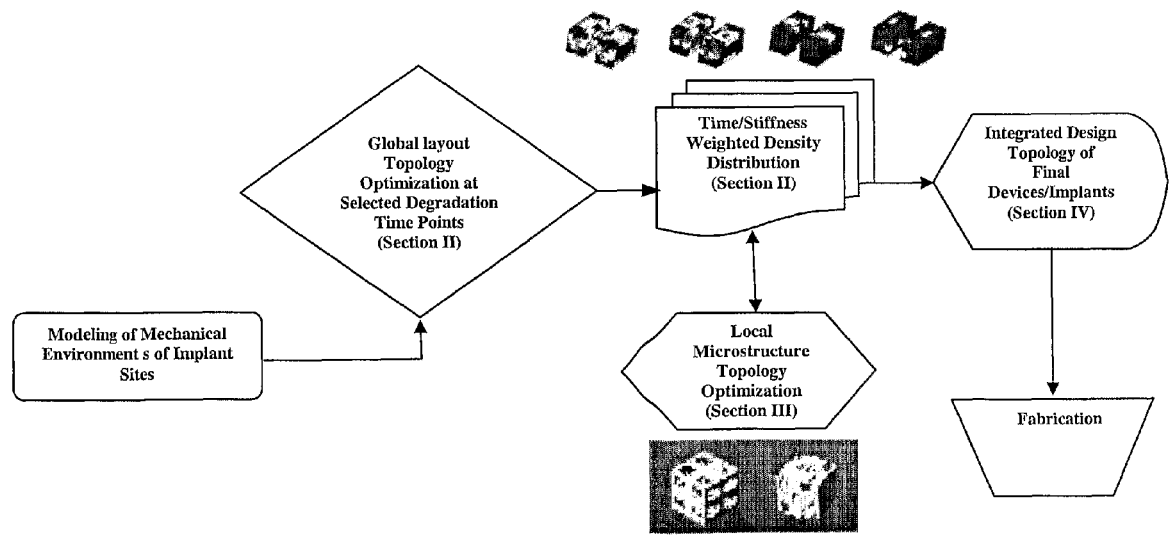
FIG. 18

BIODEGRADABLE/BIORESORBABLE TISSUE AUGMENTATION/RECONSTRUCTION DEVICE

CROSS-REFERENCE TO RELATED APPLICATIONS

This application claims the benefit of U.S. Provisional Application No. 60/527,455, filed on Dec. 5, 2003. The disclosure of the above application is incorporated herein by reference.

GOVERNMENT RIGHTS

This invention was made with government support under Grant Nos. DE13416, DE13608 awarded by the National Institute of Health. The Government may have certain rights in the invention.

FIELD OF THE INVENTION

The present invention relates to biodegradable materials and, more particularly, relates to a method of optimizing the design of biodegradable materials.

BACKGROUND AND SUMMARY OF THE INVENTION

There is growing interest in using biodegradable materials to replace permanent materials for many reconstruction applications. Degradable materials, however, are less stiff than permanent materials and suffer further stiffness reduction through time. Merely replacing the permanent material with a degradable material in the same design may lead to early device failure.

In light of the fact that many degradable materials lose material through bulk erosion without shape change, it is a principle of the present invention that through a topology optimization method accounting for base material degradation a degradable device may be created that retains sufficient stiffness through the degradation process. The optimization method of the present invention creates a density distribution map for selected time points during degradation. These different density distributions are then linearly superposed using both time and degraded base stiffness weighting factors.

According to the principles of the present invention, the present method is applied to design a degradable spinal fusion cage device from poly(propylene fumarate)/beta-tricalcium phosphate (PPF/β-TCP). However, the method is applicable for designing with any degradable material, such as but not limited to polylactic acid, polyglycolic acid, polycaprolactone, polyanhydride and tri-calcium phosphate.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 6 is a perspective view of an L4-L5 segmental level of lumbar spine model for use in processing topology optimization;

FIGS. 7a-d are block configurations of density distributions at desired time points during degradation based on poly (propylene fumarate)/beta tricalcium phosphate at (a) t=0T, E=1 GPa, (b) t=0.5T, E=875 MPa, (c) t=0.55T, E=780 Mpa, and (d) t=0.85T, E=250 Mpa, wherein T represents the total degradation duration and where the grey and lighter colors represents the most solid region and the black represents the most void;

FIG. 8 is a schematic representation of a microstructure of composite material categorized in ranks represent length scales;

FIG. 9 is a schematic representation of microstructures having differing scales;

FIGS. 16a-b are perspective views illustrating the microstructure design of 35% volume fraction and 55%, respectively;

FIGS. 17a-b are various views illustrating the biodegradable PPF/β-TCP spine interbody fusion cages according to the principles of the present invention, wherein (a) represents a cage designed by integrated topology optimization method without material density weighting and (b) represents a cage designed by integrated topology optimization method without material density weighting;

FIG. 18 is another flow chart illustrating the design process of the present invention;

DETAILED DESCRIPTION OF THE PREFERRED EMBODIMENT

The following description of the preferred embodiment is merely exemplary in nature and is in no way intended to limit the invention, its application, or uses. For instance, the method of the present invention is useful in designing with any degradable material, such as but not limited to polylactic acid, polyglycolic acid, polycaprolactone, polyanhydride and tri-calcium phosphate.

I. CURRENT TRENDS AND DESIGN TYPES OF BIODEGRADABLE/BIORESORBABLE TISSUE AUGMENTATION/RECONSTRUCTION DEVICES

Figure 1:
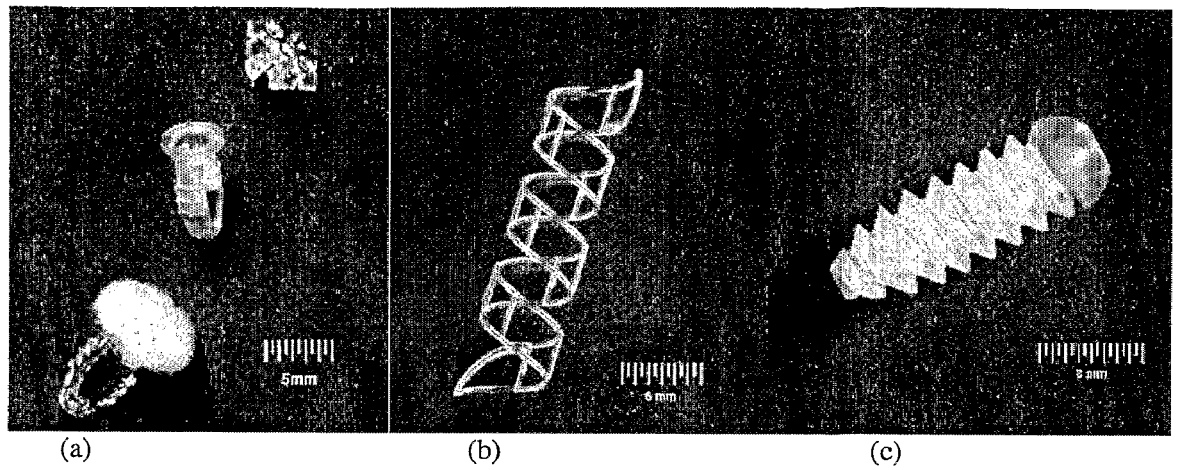
FIG. 1a is a perspective view of a bioabsorbable tissue augmentation/reconstruction device according to the prior art in the form of an "ACRU/ACRS" cartilage repair unit.
FIG. 1b is a perspective view of a bioabsorbable tissue augmentation/reconstruction device according to the prior art in the form of a Hybrid PLA/TMC intravascular stent prototype.
FIG. 1c is a perspective view of a bioabsorbable tissue augmentation/reconstruction device according to the prior art in the form of a PLA 8 mm Bio-Interference Screw.

The use of biodegradable material for tissue augmentation/reconstruction devices has become increasing prevalent to facilitate tissue regeneration and improve integration with host tissues. The concept extended from previous laboratory-scale scaffold implantations to current focuses on the application of devices such as cartilage repair units, rotator cuff anchors, intravascular stents, bone screws and plates made with poly(DL-lactic acid) or poly(L-lactic acid) (FIGS. 1a, 1b, and 1c). However, simply replacing the base material from the original design with biodegradable polymers may not be appropriate, especially for the development of load bearing devices in joint reconstructions and spine arthrodeses since degradable materials typically have less stiffness and strength than non-degradable materials. Furthermore, this stiffness and strength will degrade over time, further reducing the mechanical competency of the device. The goal is to retain adequate stiffness and strength until tissue regeneration is sufficient for the tissue to assume load bearing function.

Figure 2:
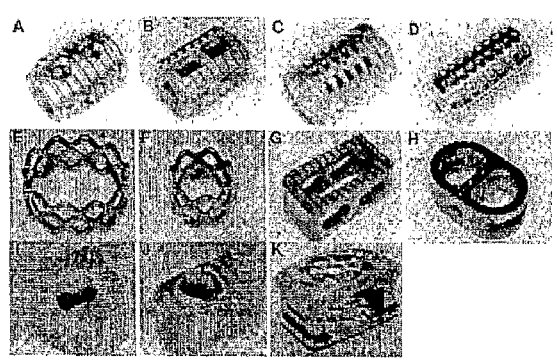
FIG. 2a is a perspective view of an interbody fusion device according to the prior art in the form of a BAK device titanium threaded cage.
FIG. 2b is a perspective view of an interbody fusion device according to the prior art in the form of a BAK Proximity, titanium threaded cage
FIG. 2c is a perspective view of an interbody fusion device according to the prior art in the form of a RAY TFC, titanium threaded cage
FIG. 2d is a perspective view of an interbody fusion device according to the prior art in the form of a Danek TIBFD, stainless steel threaded cage
FIG. 2e is a perspective view of an interbody fusion device according to the prior art in the form of a single oval Harms, titanium cylindrical mesh cage.
FIG. 2f is a perspective view of an interbody fusion device according to the prior art in the form of a double oval Harms, titanium cylindrical mesh cage.
FIG. 2g is a perspective view of an interbody fusion device according to the prior art in the form of a Brantigan PLIF, carbon fiber rectangular cage.
FIG. 2h is a perspective view of an interbody fusion device according to the prior art in the form of a Brantigan ALIF, carbon cylindrical rectangular cage.
FIG. 2i is a perspective view of an interbody fusion device according to the prior art in the form of a femoral ring allograft, sliced femoral shaft.
FIG. 2j is a perspective view of an interbody fusion device according to the prior art in the form of a bone dowel-shaped allograft with one hole.
FIG. 2k is a perspective view of an interbody fusion device according to the prior art in the form of a InFix device, titanium cylindrical implant.
Figure 3:
FIG. 3 is a perspective view of an interbody fusion device according to the prior art having a wedged design.

Implants should be designed to provide sufficient stiffness for tissue regeneration and reunion to occur before degradation. A prime example of the importance of device stiffness is spinal fusion cage design. Conventional designs of the spinal interbody fusion cages have mainly focused on providing immediate strength to maintain disc height and shielding the bone grafts within the cage. Therefore, the geometrical features of these conventional designs show little distinction from each other and most of them fall into a category of a pipe shape with thick shells as outer walls as well as a hollow interior space that brackets the fill of grafting materials (FIG. 2). Further division is defined by the threaded and non-threaded anchorage mechanism that cage devices rely on to form rigid bonds with vertebral bodies. Threaded designs may be utilized along the entirely outer surface for cylindrical cages, whereas they are distributed only on two collateral sides perpendicular to the insertion plane and later wedged into the endplates of the vertebral bodies (FIG. 3). These hollow pipe designs guarantee sufficient reconstruction stiffness in arthrodesis and play a substantial role in stability for motion segments postoperatively. However, this concept will not remain true once degradable polymers replace metallic materials in the same design. The original designed architectures will only perform as they are proposed when these devices are made with permanent materials such as metallic alloys.

Another major concern for using metallic implants is that the enormously high magnitude of the stiffness compared to bone tissue may shield an implanted graft or ingrown bone tissue from sufficient mechanical stimulus, (known as "stress-shielding") thus increasing the risk for decreased mineralization and bone resorption. This effect is seen in hip joint arthroplasties where significant bone loss around the hip stem is seen due to stress shielding. Long-term follow-up of the lumbar spine arthrodesis also indicates decreased mineralization inside the cage due to stress shielding.

Figure 4:
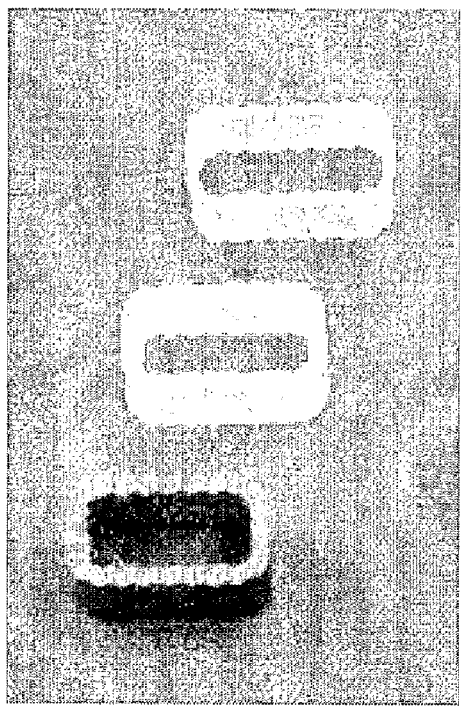
FIG. 4 is a perspective view of three poly-L-lactic acid (PLLA) interbody fusion cages.
Figure 5:
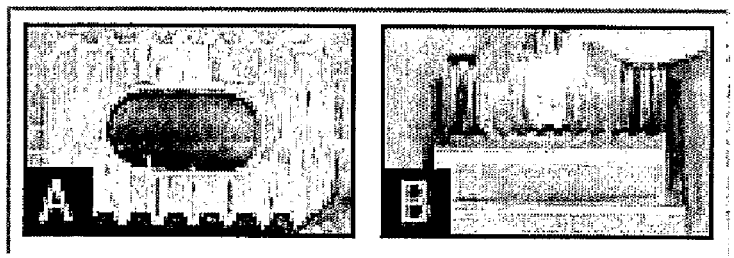
FIG. 5a is a perspective view of a 70/30 D,L-PLa interbody fusion device prior to implantation.
FIG. 5b is a perspective view of a Iliac crest autograft or rhBMP-2 on a collagen sponge packed into a thru-growth slot of the device.

Recently, poly(alpha-hydroxy esters) have been investigated as resorbable interbody fusion cages (FIGS. 4 and 5). Base material replacement without changing cage design demonstrated that reduced stiffness of the resorbable cages significantly improved fusion compared to the titanium cage when implanted in sheep. However, there is still concern that degradable spine cages will lack sufficient load bearing capability, especially given the fact that cages will lose stiffness and strength over time. In addition, loads in the human spine are much higher than in sheep spine. Because the base material stiffness will undergo persistent reduction through the degradation, merely replacing a non-degradable material with a degradable material in the same design may not produce a device that retains sufficient load bearing capability.

In the present invention, the method of integrated topology optimization incorporated with weighing factor design is used to ensure that biodegradable devices have sufficient mechanical properties initially and during degradation. Prolonging stiffness through the degradation was achieved by weighting material density to compensate for reduced base material stiffness and lost structural features caused by the bulk erosion. This method can be applied to any degradable medical device, including but not limited to spine fusion, spine disc devices, hip and knee reconstruction devices, vascular stents, cardiac assist devices, and nerve guidance channels.

II. NEW DESIGN APPROACH OF THE INVENTION TO DEFINE REINFORCED GLOBAL MATERIAL DISTRIBUTION

There are two types of degradation mechanisms for biodegradable materials: 1) bulk erosion and 2) surface erosion. Many commonly used degradable polymers including polylactic acid, polyglycolic acid, and poly(propylene) fumarate, undergo bulk erosion. Bulk erosion under the hydrolysis mechanism in physiological environments will not dramatically change the conformation but will decrease the molecular weight gradually during the degradation process. Therefore, the strength and stiffness decays even though the shape and volume do not change significantly. Based on the phenomenon, the approach that tends to utilize the structural reinforcement will have minor contributions to the entire integrity especially at the later stage of the degradation.

It's a principle of the present invention to design biodegradable/bioresorbable tissue augmentation/reconstruction devices such that these devices fulfill the multiple requirements of initial mechanical support, scaffolding for vascular supply and ingrown tissue, porous architecture for biofactor delivery as well as the sufficient residual stiffness through the degradation process to form new constructs with growing tissues. Therefore, a specific design approach will be required for degradable devices such that the stiffness satisfies load bearing requirements at time 0 (initial implantation). Sufficient stiffness must also be maintained through degradation until devices are fully integrated with or replaced by new tissue. This design technique will allow better control of material mechanical properties during the degradation process to better match the increasing mechanical properties of regenerating tissue.

Spinal fusion cages are a prime example of a device that needs to meet multiple requirements for load bearing and tissue regeneration. A suitable design for spine interbody fusion cages needs to limit displacements for stability, allow sufficient strain energy density transfer to ingrown bone to reduce stress shielding, and achieve desired porosity for tissue ingrowth. These objectives must even be met at each time during the degradation process when adopting degradable materials. The replacement of current permanent materials such as metals or carbon fibers with the degradable polymer reduces the stress shielding environment, but the higher compliance of degradable materials coupled with the continual stiffness reduction due to degradation will lead to insufficient load bearing capabilities if no compensation mechanism is incorporated in the initial design. Therefore, the design for a biodegradable spine interbody fusion cage should also take into account the maintenance of sufficient load bearings through the degradation.

According to the principles of the present invention, biodegradable devices are provided that use integrated local/global topology optimization to incorporate the degradation profile of any degradable material. In topology optimization, the design is discretized into finite elements, and each element will contain a predicted material density between 0 and 1. In the degradation design, the density in each element is weighted by the degradation profile. By altering the material weights in each element by applying two weighting factors, the weighted material density in each element within the global optimized topology will compensate for the loss of the degraded material from the original designs and retain sufficient stiffness through the degradation process. The two weighting factors are 1) time lasting factor: defined as (total degradation period—time of selective point)/total degradation period. This factor accounts for the influence of the time past implantation on reinforcement of the scaffold architecture. 2) degrading modulus factor: defined as reduced modulus at the selected time divided by the original modulus. The factor indicates the weight percentage of the original material equivalent to the superposed material densities based on the degrading modulus at selected time points. The two factors have been introduced according to the lasting time of the degrading material and the reduced base stiffness of the material at selected time points during the degradation process. These two factors together can utilize the superposed material for the reinforcement in a more efficient manner since they take both the degree of modulus reduction and the time past implantation into account. As time proceeds further past implantation, tissue ingrowth will begin to carry load, reducing the need for scaffold structure. The weighted material distribution can reinforce the stiffness at the regions that require denser material to provide sufficient load bearing especially when the base material stiffness is reduced due to the bulk erosion. Thus, the weighting process produces designs where high load bearing regions are reinforced to compensate for subsequent stiffness degradation due to bulk erosion.

For biodegradable/bioresorbable tissue augmentation/reconstruction devices, the design should balance requirements of sufficient stability, compliance to avoid stress shielding and porosity for biofactor delivery. In addition, sufficient stiffness must also be maintained through degradation until devices are fully integrated with or replaced by new tissue. Requirements of stability, reduced stress shielding, and porosity for biofactor delivery together with the need to balance these requirements through the degradation period present a number of conflicting design alternatives. Stability requires a denser material while compliance and biofactor delivery require greater porosity. Achieving a balanced design requires an optimization approach. Specifically, it is desired to create a material layout such that stability, compliance and porosity requirements can be optimally balanced while at the same time accounting for material degradation. To this end, a unique two scale topology optimization approach is utilized to create the optimal material layout for desired stability, compliance and porosity. The macroscopic or 1st scale topology optimization solution provides the general density and location of material within the implant site to limit the displacement under applied load for desired stability with a constraint to enforce the desired porosity. The microscopic or 2nd scale topology optimization approach gives the specific microstructure design that achieves a desired compliance while matching the predicted volume fraction of the macroscopic or 1st level topology optimization. The weighting process may be applied at either the macroscopic or microscopic design scale, or at both scales.

To meet the objectives mentioned above for biodegradable/bioresorbable tissue augmentation/reconstruction devices, the macroscopic or 1st scale topology optimization is used to design the material layout for selected time steps during the degradation process. The design domain for any biodegradable/bioresorbable tissue augmentation/reconstruction device can be defined with arbitrary shapes according to the implant size, anatomic geometry, and/or disease/injury requirement. The optimal material distribution through out the entire design domain is computed using topology optimization. The effective modulus is interpreted by the density method as Eijkl=XpEijkl0 to indicate the solid, porous and void regions, where Eijkl represents the effective modulus of each finite element, Xp is the fraction of the material and the base material property is Eijkl0. This weighting method is used since a degrading material must have greater density at time 0 than an equally stiff non-degrading material to retain stiffness post-implantation that meets desired design objectives. Therefore, the optimal density distribution for the degradable device material is created by superposing the multiple time optimal densities weighted by a time lasting factor Twt=(Ttotal−Tcurrent)/Ttotal and degrading modulus factor Ewt=Et/E0 as Xpw=Σ $W_t X_{pt} T_{wt} E_{wt}$, where Xpw is the final fraction of the base material, Xpt is the temporary fraction of the reduced/degraded modulus corresponding to a selected time point, Wt is a generalized weighting factor that may be linear or nonlinear, and Twt, Ew are time lasting factor and degrading modulus factor for selected time points as mentioned and defined previously.

The example of a biodegradable spine interbody fusion cage design using poly(propylene fumarate)/beta tricalcium phosphate demonstrates how the disclosed approach was applied to develop a device that meets critical requirements and objectives concurrently through the degradation. A global topology optimization algorithm (Optistruct, Altair Computing, Inc.) was used to predict a global layout density under the constraint that strain at the vertebral surface were less than 8%. Two rectangular blocks as the designable components were established to represent the location of the implanted cages and the multi-directional loads of the physiological range including compression, lateral bending, torsion, and flexion-extension were applied to the constructed segment. A finite element model was then created to simulate the mechanical environment of the design domain within the disc space (FIG. 6). The optimal design of the cage topology is interpreted by block configurations of elements corresponding to the respective material density between 0 to 1 where 0 indicates void space and 1 indicates total solid element; values in between indicate corresponding material volume fraction that occupies the element space. At the selected time points through the degradation, denser topological arrangement of the material forms to reflect that more material should be placed in the structure to maintain sufficient stiffness that is gradually reduced due to the degrading base material by bulk erosion (FIG. 7). Namely, the longer time the degradable device will go through, the higher the density of the material needed initially to compensate for the degrading stiffness to maintain adequate load bearing. However, the required higher material density at the selected time will only need to be satisfied for the time period from the beginning of the selected time until the end of the degradation. Therefore, the reinforcement design is flexible to match the needed time duration, avoiding excess use of material for long degradation periods.

FIGS. 7a to 7d represent show that the reduced base material stiffness generated denser material distribution through the degradation compared to the initial topology with the original base material. The grey and lighter color indicates higher density and becomes more prevalent at later time stages as the design becomes denser to account for a reduced base material stiffness. This suggests that for biodegradable devices, it is inappropriate to design the whole architecture merely based on the initial properties as the design for devices with permanent materials. Rather, certain reinforcements should be incorporated to compensate for degrading stiffness in higher loaded regions. Weighting material densities are applied to determine the location of higher density structural reinforced regions during degradation. FIGS. 7a to 7d show the required material distributions for t=0T, 0.5T, 0.55T, 0.85T (T: degradation duration), with the effective compressive moduli of E, 0.875E, 0.78E, 0.25E, respectively. The final density of each element thus should be expressed as: Xpw=Σ XptTwtEwt, where Xpt is the temporary density level based on reduced/degraded modulus at selected time points, Ewt is the percentage of the original modulus accounting for the degraded material at the selected time point, and Xpw in this case is the final density which is equal to Xp1+Xp2×0.5× 0.875+Xp2×0.5×0.875+Xp3×0.45×0.78+Xp4×0.15×0.25.

III. MICROSTRUCTURES AS PERIODIC UNIT CELLS IN MATERIAL CONSTITUTION

A. Introduction of Microstructure Design

A drawback of the general structural layout is that it creates transitional densities other than 0 or 1. This numerical difficulty could imply that current mesh resolution cannot carry out the structure to achieve the objective function, and has been addressed as a mesh dependent problem. Different numerical techniques such as penalty schemes have been used to impel the element density to 1 or 0 under artificial material laws, which represent the element with solid (base material) or void (no material). From a material science point of view, the intermediate density values from the global topology optimization can be viewed as representing a microstructure defined at a different length scale than the global optimization. The microstructure of composite material could be categorized into different rank, defined by different length scales, and the microstructure of particular rank will be homogenized for its upper rank (FIG. 8). This physical phenomenon permits a new approach to deal with elements of intermediate density by introducing an additional rank of material design for the particular element. Instead of choosing element of global design between 1 and 0, microstructures from the base material can be obtained that can represent those elements with ambiguous intermediate densities as shown in FIG. 9. In other words, densities between 0 and 1 can be replaced with a different scale of microstructure. This microstructure will be designed using microstructure or local topology optimization techniques.

Designing materials microstructure allows creation of structures with an extremely wide range of elastic properties. For example, materials with negative Poisson's ratio (NPR), which expands transversely when subject to an applied tensile load, can be used in many applications such as fasteners and shock observers. Furthermore, in the sense of "design", one may create the material with prescribed and specified value of material properties, such as elasticity, permeability, and dynamic performance, for a specialized application within the physical manner. For the implementation of material microstructure design for elasticity, homogenization theory with periodic boundary conditions (PBC) will be used for the design domain. Moreover, in order to theoretically calculate the effective properties of material with periodic microstructure pattern, A Finite-Element based homogenization technique is utilized, (Hollister, S., J. Brennan, and N. Kikuchi, A Homogenization Sampling Procedure for Calculating Trabecular Bone Effective Stiffness and Tissue Level Stress. J. of Biomechanics, 1994. 27(4): p. 433), with the weak form of the equilibrium constitutive equation is solved numerically using Element-By-Element Preconditioning Conjugate Gradient (EBE-PCG) to obtain the effective elastic properties.

Two optimization algorithms, denoted as full topology optimization and restricted topology optimization, are introduced to perform the microstructural level design, as described in the following sections.

B. Full Topology Optimization: Microstructure Design De Novo to Achieve Elastic Properties Design material microstructure using Topology Optimization was first implemented by Sigmund, O. in 1997, and the problem can be considered as an optimal material distribution problem within the periodic design domain and solved using Sequential Linear Programming (SLP) optimization technique. A generalized optimization problem formulation can be stated as (1).

$$\min_{\chi} \ w_1 \|C_1^H - C_1^+\|_{L_2} + w_2 \|C_2^H - C_2^+\|_{L_1} + \dots \quad (1)$$

s.t.

$$C_3^H \geq C_3^+$$

Volume fraction constraints on the constituent base material

Symmetric of design domain constraints

Connectivity of structure constraints

Bounds on design variables

Figure 10:
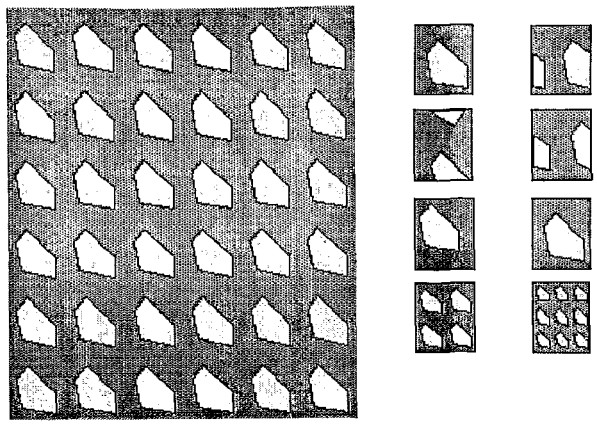
FIG. 10 is a schematic of a result illustrating the effects of periodic boundary condition.
Figure 11:
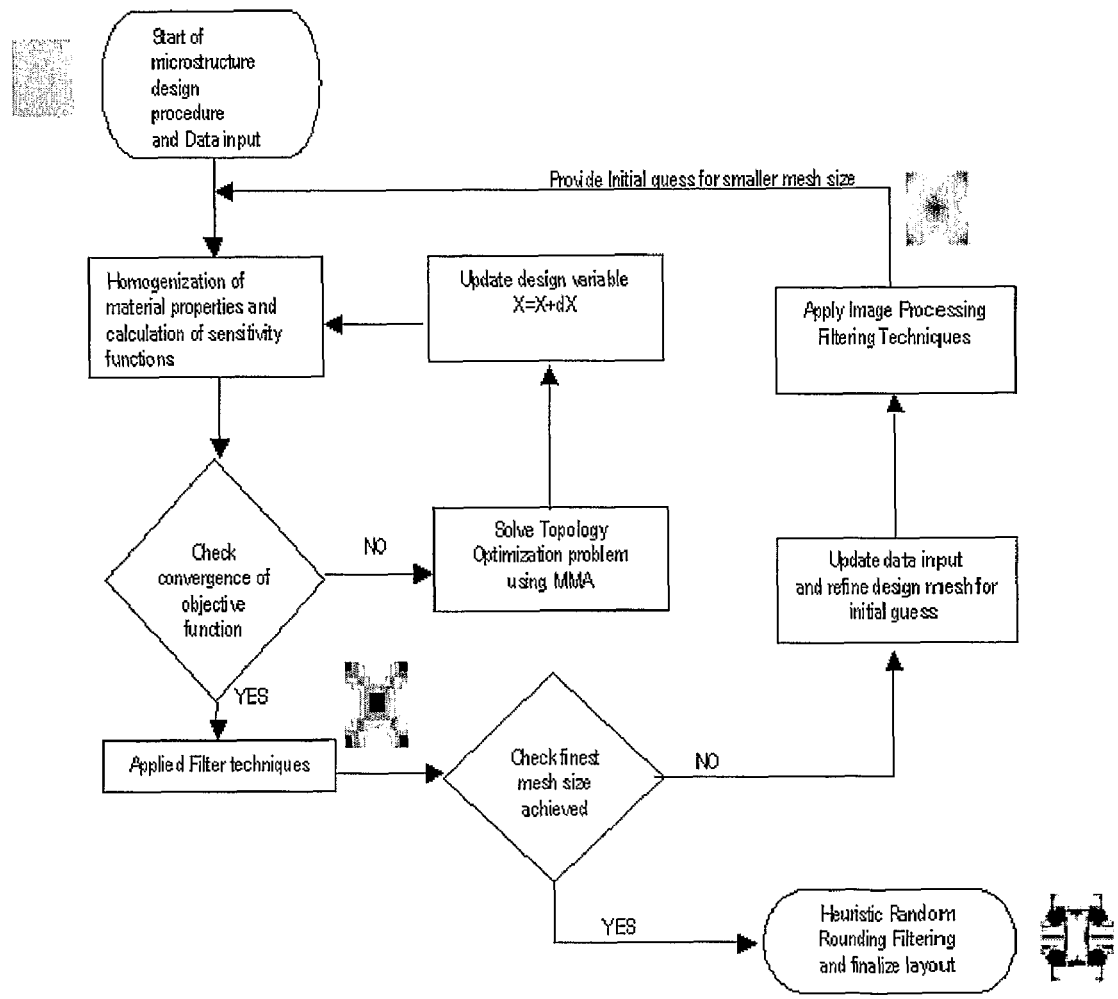
FIG. 11 is a flow chart illustrating the design process of the present invention.

C could be any material properties to be designed by minimizing the L2 norm of difference between effective properties with target properties. wi are weighting parameters. This nonlinear optimization is now solved using Method of Moving Asymptotes (MMA), which was developed Svanberg in 1987. The current approach in literature, however, suffers from numerical difficulties when implement in the 3 dimensional case. According to the present invention, two significant algorithmic enhancements have been made to address these numerical difficulties associated with full topology microstructure design. The first crucial technique was developed to deal with the design dependency of initial guess, and convergence improvement. Because of the periodic boundary condition, the optimal result is not unique (FIG. 10) and depends significantly on the initial guess of the design process. To address this issue, a low resolution mesh with homogeneous density is used first as an initial guess in the optimization process. This problem is then solved, and the resulting solution is meshed at a much finer resolution and used as an initial guess for the next set of iterations. The process ends when the best resolution is reached and converged. The detail design procedure can be illustrated in flow chart (FIG. 11).

The second enhancement involves application of image processing techniques during the topology optimization in order to eliminate checkerboard density pattern. The element density is smoothed with surrounding elements using a Gaussian smoothing filter and also a connectivity filter within each optimization iteration. After elimination of checkerboarding, or rapid fluctuation in density over short scales, the final microstructure design will still have transitional density ranging between 0 and 1, and to minimize the impact of final filtering, a heuristic based random rounding technique is developed. From the idea of integer programming, the density distribution in the design domain can also be considered as probability distribution for discrete optimization, thereby providing infinite final design generate from the probability table to which the best one that satisfy all the design criteria will be chosen to become the optimal microstructure layout.

C. Restricted Topology Optimization: Microstructure Design Assuming a Priori Topology to Achieve Elastic Properties Alternative Microstructure Options-Size Optimization (Restriction Design)

Figure 12:
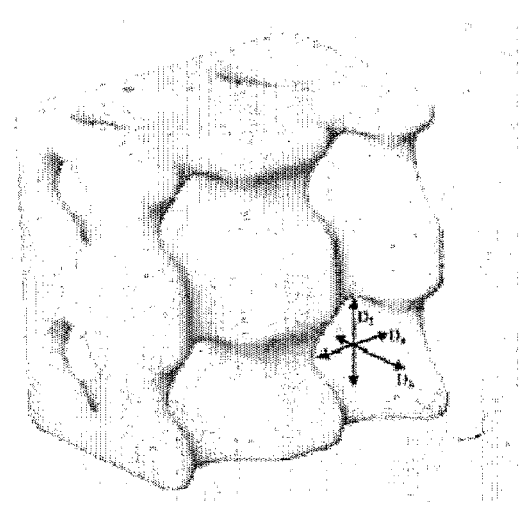
FIG. 12 is a cutaway illustrating the basic unit cell structure of interconnecting orthogonal cylinders wherein the pores are assumed to fill with regenerate tissue.

Another approach to define the microstructure of the periodic unit cell is to assume an initial topology with a restricted number of design variables describing the topology. For example, one possible design is that of interconnecting cylindrical pores, where the design variables are the pore diameters (FIG. 12). In this approach, stiffness was chosen to represent scaffold function and porosity represented the scaffold's capability to enhance tissue regeneration. This can be further divided into two design options: if the primary goal is to design a scaffold such that the scaffold itself and regenerate tissue match desired mechanical properties while maintaining a base level of porosity, the optimal design problem, denoted as the stiffness design, can be written as Objective Function:

$$\min_{E^{scaffold}, d_1, d_2, d_3} \left\{ \sum_{i=1}^{n} \left( \frac{C_i^{bone\ eff} - C_i^{tissue\ eff}}{C_i^{bone\ eff}} \right)^2 + \sum_{i=1}^{n} \left( \frac{C_i^{bone\ eff} - C_i^{scaffold\ eff}}{C_i^{bone\ eff}} \right)^2 \right\},$$

where n=1–9.
Constraints:
$d_1, d_2, d_3 \leq 900$ μm,
$d_1, d_2, d_3 \geq 300$ μm, $$\frac{V_{pore}}{V_{total}} \geq \% \ \text{Porosity},$$

$E^{scaffold} \geq E_{min}$,
$E^{scaffold} \leq E_{max}$, where design variables include $E^{scaffold}$, the scaffold base material Young's modulus and d1, d2, and d3, the three cylinder diameters. $C^{bone\ eff}$ is the effective stiffness of the target bone, $C^{tissue\ eff}$ is the regenerate tissue effective stiffness, $C^{scaffold\ eff}$ is the scaffold effective stiffness. Thus the approach generates the structural interpretation consisting of three cylindrical chambers with computed diameters and the design modulus of corresponding configuration.

Instead, if the purpose of the design is to preserve large porosity for vascularization, plus both scaffold and regenerate tissue stiffness are maintained within an acceptable range, then the optimization problem denoted as the porosity design can be written as Objective Function:

$$\max_{E^{scaffold}, d_1, d_2, d_3} \frac{V_{pore}}{V_{total}}.$$

Figure 13:
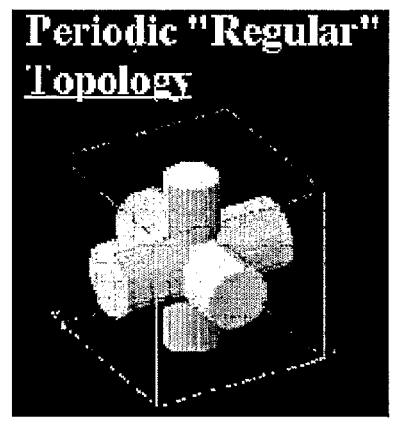
FIG. 13 is a topology of interconnecting cylinders constructing internal pore spaces.

Constraints:
$\alpha_1 C_i^{bone\ eff} \leq C_i^{tissue\ eff} \leq \alpha_2 C_i^{bone\ eff}$
where i=1–9; $\alpha_2 > \alpha_1$,
$\beta_1 C_i^{bone\ eff} \leq C_i^{scaffold\ eff} \leq \beta_2 C_i^{bone\ eff}$
where i=1–9; $\beta_2 > \beta_1$,
$d_1, d_2, d_3 \leq 900$ μm,
$d_1, d_2, d_3 \geq 300$ μm,
$E^{scaffold} \geq E_{min}$,
$E^{scaffold} \leq E_{max}$, where α1, α2, β1, and β2 are a scaling factors used to bound the scaffold and regenerate tissue effective stiffness and the variables are as defined above. Again, the computed design variable defines the final topology of the interconnecting channels by three cylindrical chambers with three diameters in the periodic unit cell shown in FIG. 13.

Figure 14:
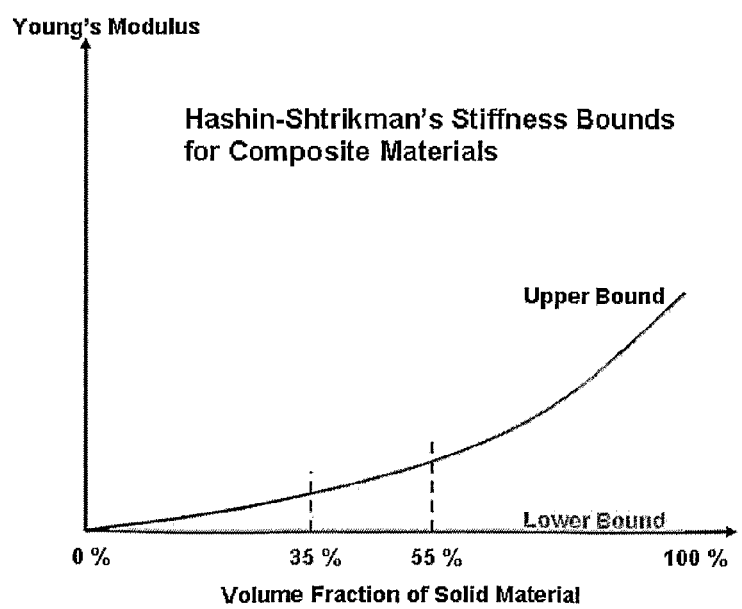
FIG. 14 is a graph illustrating the Hashin-Shtrikman's stiffness bounds for composite materials.

D. Designed Architectures to Interpret Ambiguous Density Distributions in Global Topology Degradation Optimized Designs It should be understood that once one can design material microstructure for specified properties, one can then deal with the transitional density range from the global topology optimization result. For this special spinal cage design case, the elasticity properties of materials should be considered. The upper bound and lower bound of elasticity of composite material were obtained theoretically, which means for a particular volume fraction (or porosity), there is an upper bound and lower bound of stiffness an isotropic composite can achieve, or for a particular elasticity property, there is an upper bound and lower bound of composite volume fraction to achieve, as illustrated in FIG. 14. This provides two alternative ways to interpret the global topology density prediction. For instance, assuming a global element with 0.5 density value—(1) first, the element can be interpreted to have a unique microstructure with 50% volume fraction and the objective material properties for microstructure design could be the upper or lower Hashin-Shtrikman bound depending on whether the global structure design should to have extreme stiffness or compliance properties for that particular element. (2) Second, an alternative interpretation is that considered the element could have specified anisotropic effective properties, and the microstructure is designed is to achieved these particular properties with the smallest or largest volume fraction.

E. Defined Interconnected Channels with Carriers for Biofactor Delivery

The microstructure design generates the interconnecting network of channels that define the biofactor delivery domain. The biofactors could include cell, genes, proteins or any combination of the three. The carriers could include hydrogels or polymers cast into these channels to release viable progenitor cells, genes or growth factors to achieve local bone tissue formation. Interconnecting channels can also provide favorable environments for vascularization as they provide conduits for angiogenesis and mass transportation to maintain functions of new-forming tissues. Channels confined by surrounding microstructures also imply that the ingrowth bone can receive direct mechanical stimulation transferred by struts of these microstructures, reducing stress shielding.

IV. INTEGRATION OF GLOBAL LAYOUT AND LOCAL MICROSTRUCTURE OPTIMAL TOPOLOGY

The integrated global and microstructure topology optimization approach is used to define the final architecture of biodegradable/bioresorbable tissue augmentation/reconstruction devices that meets design requirements of sufficient stability, compliance to avoid stress shielding and porosity for biofactor delivery, while the sufficient stiffness is also maintained through degradation until devices are fully integrated with or replaced by new tissue. The global topology optimization algorithm is used to generate global density distribution under physiologic loading. Immediate stability is addressed by constraining the total displacement at the implant sites to be less than a desired target. Total porosity for biofactor delivery and sufficient compliance to avoid stress shielding is input as a constraint for the global optimization at each selected time point through the degradation. The result is a global volume fraction distribution that also considers the reinforcement for the stiffness reduced through degradation by linearly superposing different density distributions at selected time points using both time and degraded base stiffness weighting factors. The layout density threshold was then processed to segment the entire interconnected architecture to four separate material phases of complete solid, high percentage solid, low percentage solid, and completely void (0% material) regions to match the target porosities of the microstructure design while maintaining sufficient stiffness and acceptable connectivity. Note that the global material layout only provides a porosity and does not define the topology of the porous microstructure. To further define the microstructure, a local microstructural topology optimization method was used to generate periodic microstructures for the high percentage and low percentage solid regions that achieved Hashin-Shtrikman stiffness bounds for porous isotropic materials. The entire device design could then be generated by alternating periodic microstructures within the global density layout. The density of the global layout served as a flag to assign the microstructural topology. The overall volume fraction was closely held at that of the original global layout optimal topology after the replacement of original global elements with designed microstructures. The resulting porous cage architecture can also serve a dual purpose as a delivery vehicle that would be appropriate for therapeutic cell transplantation.

A schematic flow chart of the design process can be seen in FIG. 18. For further description of the present invention, please refer to attached Exhibit A, which is provided originally in color.

V. RESULTS

Figure 15:
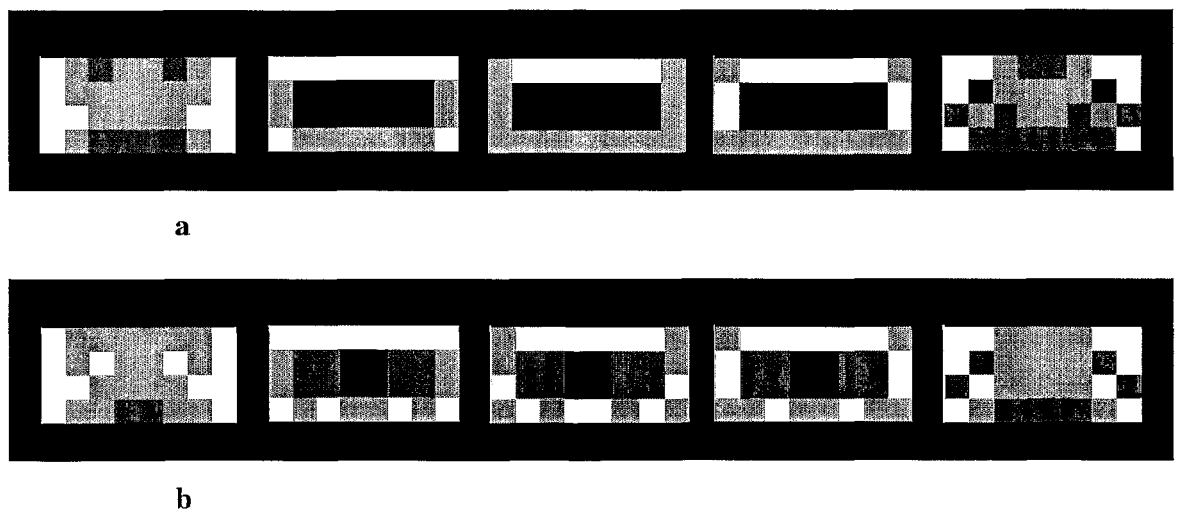
FIGS. 15a-b are layout density segmented into four phases after threshold processing wherein dark gray and light gray regions are later replaced by corresponding microstructure of 55% and 35% volume fraction, respectively. (a) Layout density distribution on each layer of the spine cage design without material density weighting. (b) Layout density distribution on each layer of the spine cage design applying the material density weighting with consequent material density distributions of reduced base material stiffness.

Our prototype demonstrates an example of applying the design methodology of the present invention for biodegradable devices to spine interbody fusion cage design. The cage design domain was constructed with 8 by 5 by 4 elements, the size of which is exactly the same as the microstructure dimension. The base material for the example is a biodegradable polymer composite of poly(propylene fumarate)/β-tricalcium phosphate) (PPF/β-TCP). A composite material of poly(propylene fumarate)/beta-tricalcium phosphate was selected as the exemplary biodegradable polymer since it has been proved to be osteoconductive and upon degradation yields primarily fumaric acid and propylene glycol that can be removed by normal metabolic pathways. Optimal topology for each selected time points was represented in density distribution in block configuration as shown in FIG. 7. Note that it is reasonable that the structure designed for degradation will be denser than other structures as the added material is needed to compensate for the reduced stiffness over time. The layout density threshold was processed to segment the entire interconnected architecture to four separate material phases of 100% solid, 55% solid, 35% solid, and completely void (0% material) so that the layout of each layer is composed of three values of grayscale referred to the corresponding regions. FIG. 15(a) shows the segmentation process on the initial density distribution at time 0 without applying the material density weighting. When applying the material density weighting with consequent material density distributions of reduced base material stiffness, certain regions were reinforced with weighted material density shown in the segmented layout as in FIG. 15(b). The local microstructural topology optimization method then generated periodic microstructures for the 55% and 35% solid regions (FIG. 16).

The prototype of the designed cage was achieved by automatically converting the image-design data to a surface representation in .STL format. The image-design data was also converted to contour .SLF format. The .STL and contour was then loaded in 3-D printing machine for the preparation of wax molds. Poly(propylene fumarate) (Mn=1200) cross-linked by N-vinyl pyrrolidone combined with beta-tricalcium phosphate (PPF/β-TCP) was cast in the prepared molds. Final prototypes are illustrated in FIG. 17 for both designs with and without the material weighting. The actual size for the prototype is 24 mm×15 mm×12 mm, with 5 and 4 microstructures making up the cross-sectional areas and 8 on long one.

The degradation characterization experiment to verify the invention has been conducted for three cage designs fabricated (N=24 per design) with poly(propylene fumarate) cross-linked by N-vinyl pyrrolidone combined with beta-tricalcium phosphate. These designs included a standard threaded cage (standard: CON Cage), a cage optimized for initial properties (optimized: OS Cage), and a cage optimized accounting for degradation (degrading optimized: OS Deg Cage). Samples from each group underwent degradation under the conditions described in the ISO13781 standard. Micro-CT scanning, mechanical testing, and weigh loss measurement were conducted to investigate the degrading properties at 0, 3, 6, and 12 weeks.

Figure 19:
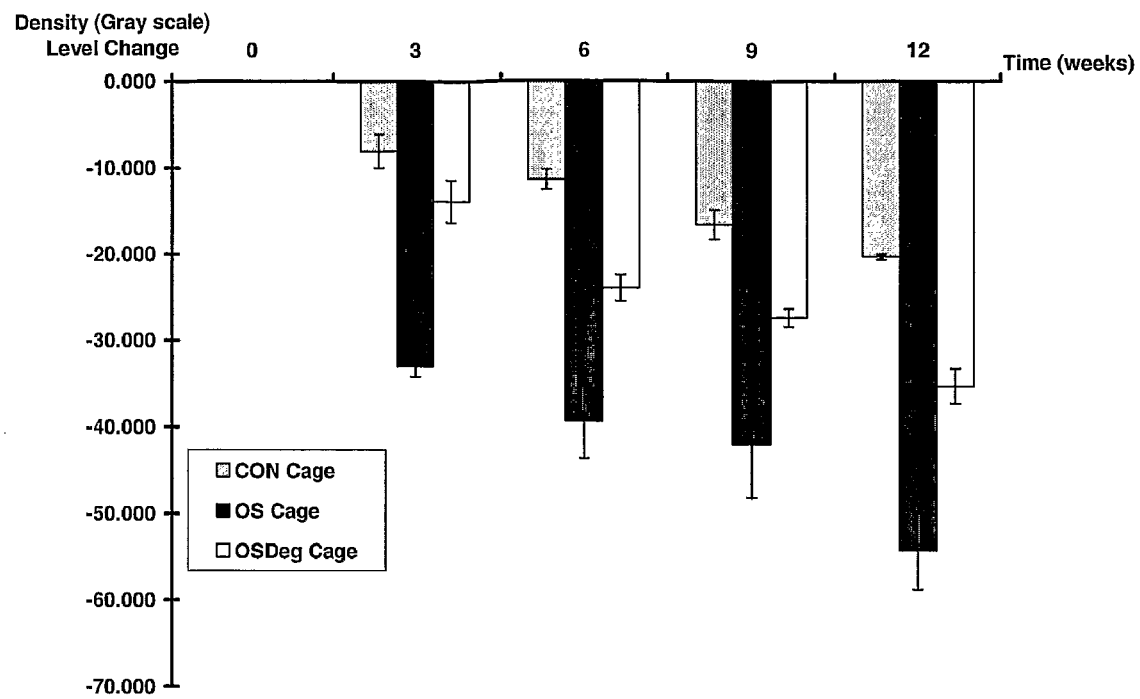
FIG. 19 is a graph illustrating the density (grayscale) level change of consecutive micro-CT scan on each cage design at selected time points through the degradation, wherein error bars indicate means±standard deviation for n=3.

The scanned images of each design at each selected time point were compared. Degraded elements on the image can be clearly viewed as pixels with lower densities at the end of the degradation (12 weeks). The geometric features and the entire shape of three cages remained intact, indicating the bulk erosion process that the degradation mechanism did not change the geometry of the design, but did cause the molecular weight and mass loss along with the degradation process. FIG. 19 shows that CON cage presented the least density change while OS cage lost more density than the CON and OSDeg design. The density decrease of the OSDeg design fell in between those of CON and OS cage designs.

Figure 20:
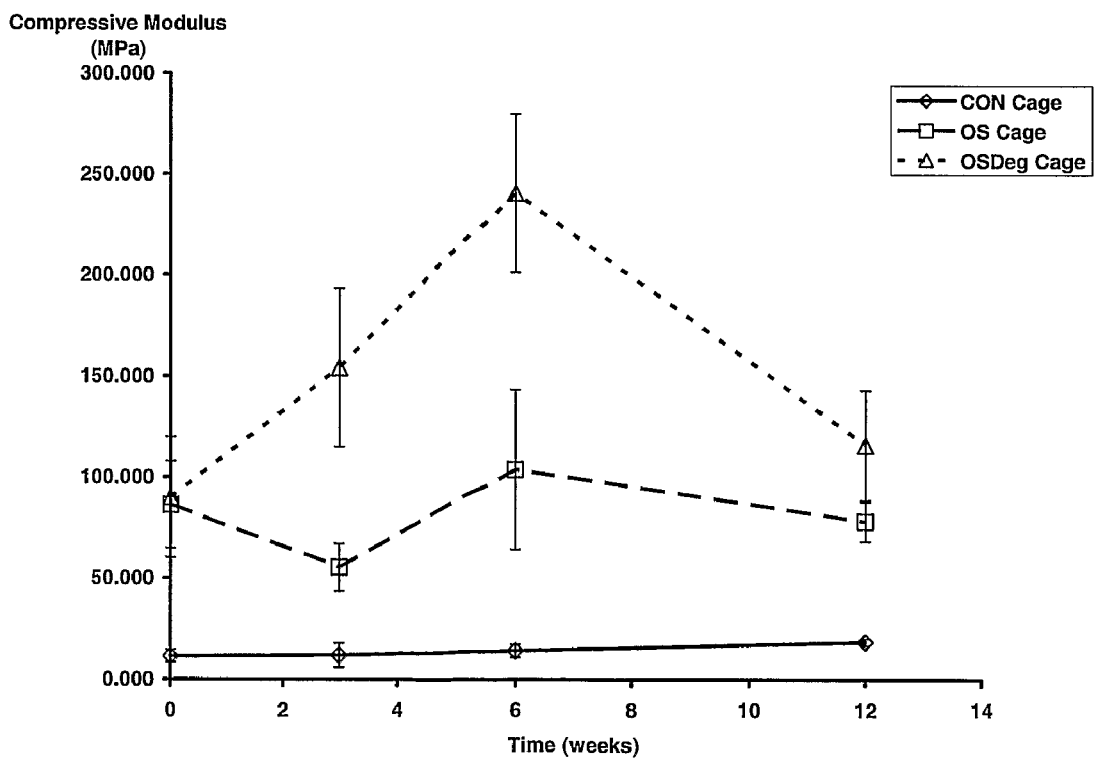
FIG. 20 is a graph illustrating a comparison of compressive modulus of each cage design at selected time points through the degradation, wherein volume fractions of the material in each design are 15% for CON cage, 55% for OS cage, and 65% for OSDeg cage, respectively, and error bars indicate means±standard deviation for n=6.

The data collected from the MTS compression test through the degradation are shown in FIG. 20. The chart shows the compressive modulus at our selected time points through the degradation of each design and their corresponding volume fractions of PPF/β-TCP composite material. It is intuitively true from the stiffness profile that a design with more volume fraction will have higher stiffness and strength. However, in addition to increased mass, the 3D spatial arrangement of material will also significantly influence stiffness and strength. In OS cage design, the initial drop of the modulus at 3 weeks followed by the increasing stiffness matched the behavior of porous PPF/β-TCP composite scaffolds that were shown in previous studies under both in vitro and in vivo conditions by Yaszemski et al. and Peter et al. The peak value of the compressive modulus of OS cage reaches 100 MPa at 6 weeks, which is close to the trabecular bone modulus. However, the overall mechanical performance of OS cage design is still below the requirement for being capable of providing load bearings to maintain the disc height at the early stage in spine arthrodesis.

In CON cage design, the compressive modulus was consistent throughout the degradation, which suggests that the two total solid endplates in the entire structure may take the major responsibility for the load bearing capacity, and it is reasonable from this observation that the total solid regions may take longer time to degrade and lose effective stiffness than the porous regions. Nevertheless, the result still shows that the overall compressive modulus of less than 20 MPa in CON cage design is far below the requirement to provide mechanical strength as a resistance for external loads on the spine segments.

Interestingly, the compressive modulus in OSDeg increased until the half of the total degradation time of 12 weeks. The peak modulus was nearly 250 MPa, which is sufficient to provide load bearing to the fusion construct at the early stage before the complete fusion bony bridge forms to share loads. The result suggests that by coupling the Integrated Topology Optimization technique with the density weighting method along the degradation profile, the Degradation Topology Optimization reinforces the major load bearing elements throughout the entire cage structure. These reinforcements created by the degradation topology optimization along with the continued cross-linking of the PPF/β-TCP material provided structural stiffness after 12 weeks that was actually superior to that at time 0.

VI. CONCLUSION

Currently, biodegradable polymers have offered researchers and scientists a possible solution to the waste-disposal problems associated with traditional petroleum-derived plastics. Innovative new biomedical applications, including artificial skin, heart valves, and other organs grown on biopolymer scaffolding, are creating major opportunities for new product development and the commercial exploitation of these materials.

Biopolymers, which can be either derived from natural or synthetic materials, provide a number of advantages over traditional synthetic plastics derived from petroleum. They are biodegradable/bioabsorbable, and therefore environmentally friendly, as well as biocompatible, which makes them a suitable alternative to compounds such as silicone in medical applications. In addition to the development of biopolymer-based processes for growing artificial organs, scientists have successfully used biopolymers to create "drugs" that never enter the bloodstream, antibacterial coatings for medical devices, a microsponge technology that releases medical ingredients slowly over time, a collagen plug that revolutionizes postoperative care, and therapies based on hyaluranon, a specially tailored visco-elastic biopolymer.

The disclosed invention offers a new approach to give biopolymeric medical devices adequate mechanical performance for a variety of purposes. Biodegradable skin grafts need to provide stretch resistance before the full integration with the host parenchymal tissues, before then the reinforced material should be applied to prolong the structural integrity. Devices used to fix traumatic fractures require sustaining ultimate strength until the acceptable union occurs, but this is not easy to be achieved when utilizing biodegradable polymers. Implants for those sites with main load bearings especially need the specific designed architecture to maintain the biomechanical functions. Thus, the invention provides a general design approach to fulfill individual demand of mechanical performances for each biodegradable/bioresorbable tissue augmentation/reconstruction device.

Lastly, it should be understood that the present invention may be used in conjunction with related techniques, such as those set forth in U.S. Patent Application No. 2003/0069718 and 2003/0006534. These applications are incorporated herein by reference.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A method of designing a biodegradable/bioresorbable tissue augmentation/reconstruction device, said method comprising:
    creating a material density distribution map using a computer based on an initial design shape, said material density distribution map having discrete points;

determining a numerical weighting factor based on a predicted time-based elastic or molecular weight degradation pattern;

weighting said material density distribution map using said numerical weighting factor to determine a weighted density distribution map; and using said weight density distribution map to determine a material reinforcement to create a final design shape such that the device will retain predetermined structural properties during a material degradation lifecycle.

2. The method according to claim 1 wherein said material density distribution map is created using the computer using a technique chosen from the group consisting essentially of topology optimization, microstructure topology optimization, restricted topology optimization, image-based design, and computer-aided design techniques.

3. The method of claim 1 wherein said material density distribution map is created using the computer using topology optimization having an algorithm employed to define said material density distribution map at predetermined time points during said material degradation lifecycle.

4. The method of claim 1 wherein said material density distribution map is created using the computer using image-based design defining said material density distribution map at predetermined time points during said material degradation lifecycle.

5. The method of claim 1 wherein said material density distribution map is created using the computer using general computer aided design techniques include defining said material density distribution map at predetermined time points during said material degradation lifecycle.

6. The method according to claim 1 wherein said weighting factor is chosen from the group consistently essentially of a linear weighting factor, a nonlinear weighting factor, a time past degradation factor, and a ratio of a degraded material property to initial material property.

7. The method according to claim 6 wherein said ratio of a degraded material property to initial material property includes a ratio of a degraded modulus to an initial modulus.

8. The method according to claim 6 wherein said ratio of a degraded material property to initial material property includes a ratio of a degraded strength to an initial strength.

9. The method according to claim 6 wherein said ratio of a degraded material property to initial material property includes a ratio of a degraded thermal conductivity to an initial thermal conductivity.

10. The method according to claim 6 wherein said ratio of a degraded material property to initial material property includes a ratio of a degraded electrical conductivity to an initial electrical conductivity.

11. The method according to claim 1, further comprising: superposing said material density distribution map at predetermined time points using both time, degraded base stiffness, and said weighting factor.

12. The method according to claim 1, further comprising: superposing said material density distribution map at predetermined time points using density at a global anatomic level.

13. The method according to claim 12, further comprising: superposing said material density distribution map at predetermined time points using density at a physical size smaller than said global anatomic level.

14. The method according to claim 1 wherein said weighting said material density distribution map using a weighting factor to determine a weighted density further includes employing material degradation kinetics to enhance said material density distribution map.

15. The method according to claim 14 wherein said employing material degradation kinetics further comprises employing one chosen from the group consisting essentially of polylactic acid, polyglycolic acid, polyanhydride, polycaprolactone, tri-calcium phosphate, and hydrogels.

16. A method of manufacturing a biodegradable/bioresorbable tissue augmentation/reconstruction device, said method comprising:

defining an initial shape as elements having a predicted material density between 0 and 1;

weighting each predicted material density by a predetermined degradation profile to define a weighted material density, said degradation profile being unique to a material used;

calculating a material weight in each of said elements by applying a time lasting factor and a degrading modulus factor to said weighted material density such that high load bearing regions within the device are reinforced to compensate for subsequent stiffness degradation due to bulk erosion of the device, and manufacturing the device based on the calculated material weight.

17. The method according to claim 16, further comprising: converting said calculated material weight to surface representation prior to said manufacturing.

18. The method according to claim 17 wherein said converting said calculated material weight to surface representation includes converting said calculated material weight to a Stereo lithographic (STL) surface representation.

19. The method according to claim 17 wherein said converting said calculated material weight to surface representation includes converting said calculated material weight to a Computer Aided Design (CAD) surface.

20. The method according to claim 17 wherein said converting said calculated material weight to surface representation includes converting said calculated material weight to a wireframe representation.

* * * * *

UNITED STATES PATENT AND TRADEMARK OFFICE
CERTIFICATE OF CORRECTION

| | | |
|---|---|---|
| PATENT NO. | : 7,979,150 B2 | |
| APPLICATION NO. | : 10/581424 | |
| DATED | : July 12, 2011 | |
| INVENTOR(S) | : Chia-Ying Lin et al. | |

It is certified that error appears in the above-identified patent and that said Letters Patent is hereby corrected as shown below:

Column 2, line 17, after "cage", insert --;--.

Column 2, line 20, after "cage", insert --;--.

Column 2, line 23, after "cage", insert --;--.

Column 2, line 60, "Mpa" should be --MPa--.

Column 2, line 61, "Mpa" should be --MPa--.

Column 2, line 66, "represent" should be --representing--.

Column 3, line 63, "increasing" should be --increasingly--.

Column 7, line 1, "through out" should be --throughout--.

Column 7, line 19, "Ew" should be --Ewt--.

Column 7, line 40, "in between" should be --inbetween--.

Column 7, line 54, delete "represent".

Column 8, line 47, "observers" should be --absorbers--.

Column 9, line 28, after "developed", insert --by--.

Column 9, line 30, "implement" should be --implemented--.

Column 9, line 60, "satisfy" should be --satisfies--.

Column 10, line 62, after "are", delete "a".

Column 11, line 22, after "should", delete "to".

Column 11, line 26, "is to achieved" should be --to achieve--.

Column 11, line 32, "cell" should be --cells--.

Column 12, line 53, after "to", insert --in--.

Column 13, line 18, "weigh" should be --weight--.

Column 15, line 35, Claim 6, "consistently" should be --consisting--.

Column 16, line 44, Claim 18, "lithographic" should be --Lithographic--.

Signed and Sealed this
Eleventh Day of October, 2011

David J. Kappos
*Director of the United States Patent and Trademark Office*